United States Patent
Huberman et al.

(10) Patent No.: US 6,495,340 B2
(45) Date of Patent: Dec. 17, 2002

(54) CELL CARRIER GRIDS

(75) Inventors: Tamir Huberman, Rehovot (IL); Yal Schiffenbauer, Rosh Ha-Ayin (IL)

(73) Assignee: Medis El Ltd., Yehud (IL)

(*) Notice: Subject to any disclaimer, the term of this patent is extended or adjusted under 35 U.S.C. 154(b) by 27 days.

(21) Appl. No.: 09/886,205

(22) Filed: Jun. 22, 2001

(65) Prior Publication Data

US 2002/0094567 A1 Jul. 18, 2002

Related U.S. Application Data

(60) Provisional application No. 60/253,134, filed on Nov. 28, 2000.

(51) Int. Cl.[7] .............................. C12Q 1/24; C12Q 1/02; C12Q 1/68; C12M 1/00
(52) U.S. Cl. ............................. 435/30; 435/29; 435/6; 435/4; 435/307.1; 435/308.1
(58) Field of Search ................................ 435/30, 29, 6, 435/4, 307.1, 308.1

(56) References Cited

U.S. PATENT DOCUMENTS

| | | | | |
|---|---|---|---|---|
| 4,729,949 A | * | 3/1988 | Weinreb et al. ................ | 435/30 |
| 4,772,540 A | * | 9/1988 | Deutsch et al. ............. | 430/320 |
| 5,272,081 A | * | 12/1993 | Weinreb et al. .......... | 435/240.1 |
| 5,310,674 A | * | 5/1994 | Weinreb et al. ............. | 435/293 |
| 5,506,141 A | * | 4/1996 | Weinreb et al. .......... | 435/309.1 |
| 6,103,479 A | * | 8/2000 | Taylor ........................ | 435/7.2 |
| 2002/0094567 A1 | * | 7/2002 | Huberman et al. ...... | 435/304.2 |
| 2002/0106715 A1 | * | 8/2002 | Huberman et al. ........... | 435/33 |

* cited by examiner

Primary Examiner—Louise N. Leary
(74) Attorney, Agent, or Firm—Mark M. Friedman (57) ABSTRACT

An improved cell carrier grid. The grid is capable of containing and retaining individual living cells in an array discrete locations and includes a body that defines having an ordered array of holes arranged according to an organizational plan such that each of the holes is identifiable. Each of said holes can contain at least a portion of an individual living cell. According to some embodiments of the invention, individual cells contained within said holes reside substantially in a single focal plane so that accuracy of data collected is increased. According to some embodiments of the invention, said body is at least partially coated with a biologically active material. According to some embodiments of the invention, said body is designed and constructed such that said individual cells contained within said holes are recoverable by a recovery device.

17 Claims, 5 Drawing Sheets

CELL CARRIER GRIDS

This application claims the benefit of Provisional application Ser. No. 60/253,134, filed Nov. 28, 2000.

FIELD AND BACKGROUND OF THE INVENTION

The present invention relates to improved cell carrier grids and, more particularly, to cell carrier grids coated with biologically active materials and to cell carrier grids designed and constructed to hold cells in a single focal plane for analysis. The present invention further relates to cell carrier grids which allow recovery of individual cells based upon the results of analyses conducted thereupon.

Because of the complex nature of biological systems, it is often desirable to conduct analyses on a specific sample to compare to normative values. For example, liver enzyme levels from a specific patient compared to normative values for the same enzyme may be used to diagnose diabetes.

Further, it is often desirable to assay cells taken from a specific organ or tissue in order to diagnose a condition in a patient. In some cases, a sample may contain a physiologically mixed population of cells, only a portion of which is to be analyzed. Machines such as a fluorescence activated cell sorter (FACS) were designed, in part, to overcome this problem. However, a FACS machine cannot reassay individual cells after sorting. This limitation precludes both kinetic studies of individual cells and recovery of individual cells after assay based upon assay results.

Therefore, a number of prior art devices were patented by Weinraub et al. to address some of these issues. (U.S. Pat. Nos. 4,729,949; 5,272,081; 5,310,674; and 5,506,141)

U.S. Pat. No. 4,729,949 teaches methods and apparatus for performing analyses on individual living cells. According to the teachings of this patent, individual cells are forced into holes in a grid so that each of the cells may be individually assayed and re-assayed. The teachings of this patent do not provide means for assuring that all cells are held in a single focal plane during their residence in the grid and subsequent assay. As a result, practice of the teachings of this patent introduces inaccuracy into the measurements. In addition, the grid taught by this patent is biologically inert.

U.S. Pat. No. 5,310,674 is similar except that it teaches an ordered array of holes of two different sizes so that sorting of cells by size into two subpopulations is theoretically feasible. Teachings of this patent do not explain why a large cell will not be retained in a small hole when suction is applied therethrough.

U.S. Pat. No. 5,272,081 teaches identification and subculture of a selected subgroup of cells residing in a grid of the type taught in U.S. Pat. No. 4,729,949. Therefore, the same inherent drawbacks are present in the teachings of this patent.

U.S. Pat. No. 5,506,141 is similar to U.S. Pat. No. 4,729,949 except that it teaches that "the positions on the carrier of the holes are identifiable."

U.S. Pat. No. 4,772,540 to Deutsch et al. teaches a method of manufacture for a rigid grid resistant to mechanical distortion. Despite the added strength, grids produced according to the teachings of Deutsch do not hold cells in a single focal plane.

U.S. Pat. No. 6,103,479 issued to Taylor teaches coating of miniaturized cell arrays with biologically active compounds in conjunction with an apparatus for cell-based screening concerning the physiological response of the cells to the biologically active compounds. Teachings of this patent do not include keeping cells in a single focal plane to increase accuracy of analysis. Similarly, analysis and subsequent collection of individual cells based upon assay results is not taught by this patent.

U.S. Pat. No. 5,635,363 issued to Altman et al. teaches the use of multimeric MHC-antigen complexes to form a stable structure with T-cells. Teachings of this patent do not include binding and subsequent assay of individual T-cells in order to allow for the labeling, identification and separation of specific T cells.

There is thus a widely recognized need for, and it would be highly advantageous to have, cell carrier grids devoid of the above limitations.

SUMMARY OF THE INVENTION

According to one aspect of the present invention there is provided a cell carrier grid capable of containing and retaining individual living cells in an array of predefined discrete locations. The cell carrier grid comprises (a) a body that defines a first and a second outer surface, the body having an ordered array of holes therethrough, each of the holes communicating between the first outer surface and the second outer surface; (b) an organizational plan, the plan being applied to the positioning of the holes on the body such that a position of each of the holes is identifiable so that the holes form the array of predefined discrete locations. Each of the holes is sized to contain at least a portion of an individual living cell therewithin, in that each hole has: (i) a first cross section at the first outer surface of such dimensions that at least a portion of the individual living cell can pass through the first cross section without suffering substantial damage; (ii) a second cross section at a level intermediate between the first and the second outer surfaces of such dimensions that the individual living cell cannot pass through the second cross section; (iii) a height between the first outer surface and the level of the second cross section such that at least a portion of the individual living cell is containable within the hole, and the individual cell is retained therein. The body is designed and constructed such that the individual cells contained within the holes reside substantially in a single focal plane during analysis and accuracy of data collected from the individual cells within the holes is increased because the cells reside substantially in a single focal plane.

According to another aspect of the present invention there is provided a cell carrier grid capable of containing and retaining individual living cells in an array of predefined discrete locations, the cell carrier grid comprising; (a) a body that defines a first and a second outer surface, the body having an ordered array of holes therethrough, each of the holes communicating between the first outer surface and the second outer surface; (b) an organizational plan, the plan being applied to the positioning of the holes on the body such that a position of each of the holes is identifiable so that the holes form the array of predefined discrete locations; and (c) wherein each of the holes is sized to contain at least a portion of an individual living cell therewithin, in that each hole has (i) a first cross section at the first outer surface of such dimensions that at least a portion of the individual living cell can pass through the first cross section without suffering substantial damage; (ii) a second cross section at a level intermediate between the first and the second outer surfaces said second cross section being no greater in size than said first cross section; and (iii) a height between the first outer surface and the level of the second cross section such that at least a portion of the individual living cell is containable within the hole, and the individual cell is retained therein. The body is at least partially coated with a biologically active material.

According to yet another aspect of the present invention there is provided a cell carrier grid capable of containing and retaining individual living cells in an array of predefined discrete locations, the cell carrier grid comprising; (a) a body that defines a first and a second outer surface, the body having an ordered array of holes therethrough, each of the holes communicating between the first outer surface and the second outer surface; (b) an organizational plan, the plan being applied to the positioning of the holes on the body such that a position of each of the holes is identifiable so that the holes form the array of predefined discrete locations and (c) wherein each of the holes is sized to contain at least a portion of an individual living cell therewithin, in that each hole has (i) a first cross section at the first outer surface of such dimensions that at least a portion of the individual living cell can pass through the first cross section without suffering substantial damage; (ii) a second cross section at a level intermediate between the first and the second outer surfaces said second cross section being no greater in size than said first cross section; and (iii) a height between the first outer surface and the level of the second cross section such that at least a portion of the individual living cell is containable within the hole, and the individual cell is retained therein. The body is designed and constructed such that the individual cells contained within the holes are recoverable by a recovery device.

According to further features in preferred embodiments of the invention described below, the body is inherently rigid, such that the individual cells contained within the holes reside substantially in a single focal plane during analysis.

According to still further features in the described preferred embodiments the cell carrier grid of claim 1, wherein the body is supported by at least one support, such that the individual cells contained within the holes reside substantially in a single focal plane during analysis.

According to still further features in the described preferred embodiments the cell carrier grid further includes a holder designed and constructed to: (i) facilitate manipulation of the cell carrier grid; (ii) allow application of suction through the holes in the grid such that cells in suspension applied to the first outer surface of the grid tend to move towards and into the holes; and (iii) permit application and removal of is solutions to cells residing in the holes.

According to still further features in the described preferred embodiments the biologically active material includes at least one material selected from the group consisting of a protein, a carbohydrate, a nucleic acid, and a lipid.

According to still further features in the described preferred embodiments the protein is selected from the group consisting of an antibody, an antigen, biotin, avidin, streptavidin, an enzyme, a ligand, a receptor, a mitogen, a haptene, a multimeric MHC-antigen complex and a lectin.

According to still further features in the described preferred embodiments the nucleic acid is selected from the group consisting of DNA, RNA and derivatives thereof.

According to still further features in the described preferred embodiments the lipid is selected from the group consisting of Lysophosphatydilcholine (polar phospholipid) and OxLDL According to still further features in the described preferred embodiments the biologically active material is used to coat the body at a location selected from the group consisting of within the holes and adjacent to the holes.

According to still further features in the described preferred embodiments the biologically active material comprises at least two separate biologically active materials, each of the at least two materials applied to a portion of the holes comprising the array of predefined discrete locations.

According to still further features in the described preferred embodiments at least 20% of the individual living cell contained within a hole extends beyond a plane defined by the first outer surface to render the cell recoverable by a recovery device.

According to still further features in the described preferred embodiments wherein at least 40% of the individual living cell contained within a hole extends beyond a plane defined by the first outer surface to render the cell recoverable by a recovery device.

According to still further features in the described preferred embodiments wherein at least 50% of the individual living cell contained within a hole extends beyond a plane defined by the first outer surface to render the cell recoverable by a recovery device.

The present invention successfully addresses the shortcomings of the presently known configurations by providing cell carrier grids which are coated with biologically active materials and cell carrier grids designed and constructed to hold cells in a single focal plane for analysis. The present invention further relates to cell carrier grids which allow recovery of individual cells based upon the results of analyses conducted thereupon.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of improved cell carrier grids which can be coated with biologically active materials, can be designed and constructed to hold cells in a single focal plane for analysis and which allow recovery of individual cells based upon the results of analyses conducted thereupon.

Specifically, the present invention can be used to used to regulate a biological function in cells before or during assay, to increase the accuracy of assays performed on cells contained in the cell carrier grid and to allow recovery of individual cells based upon the results of analyses conducted thereupon.

The principles and operation of improved cell carrier grids according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
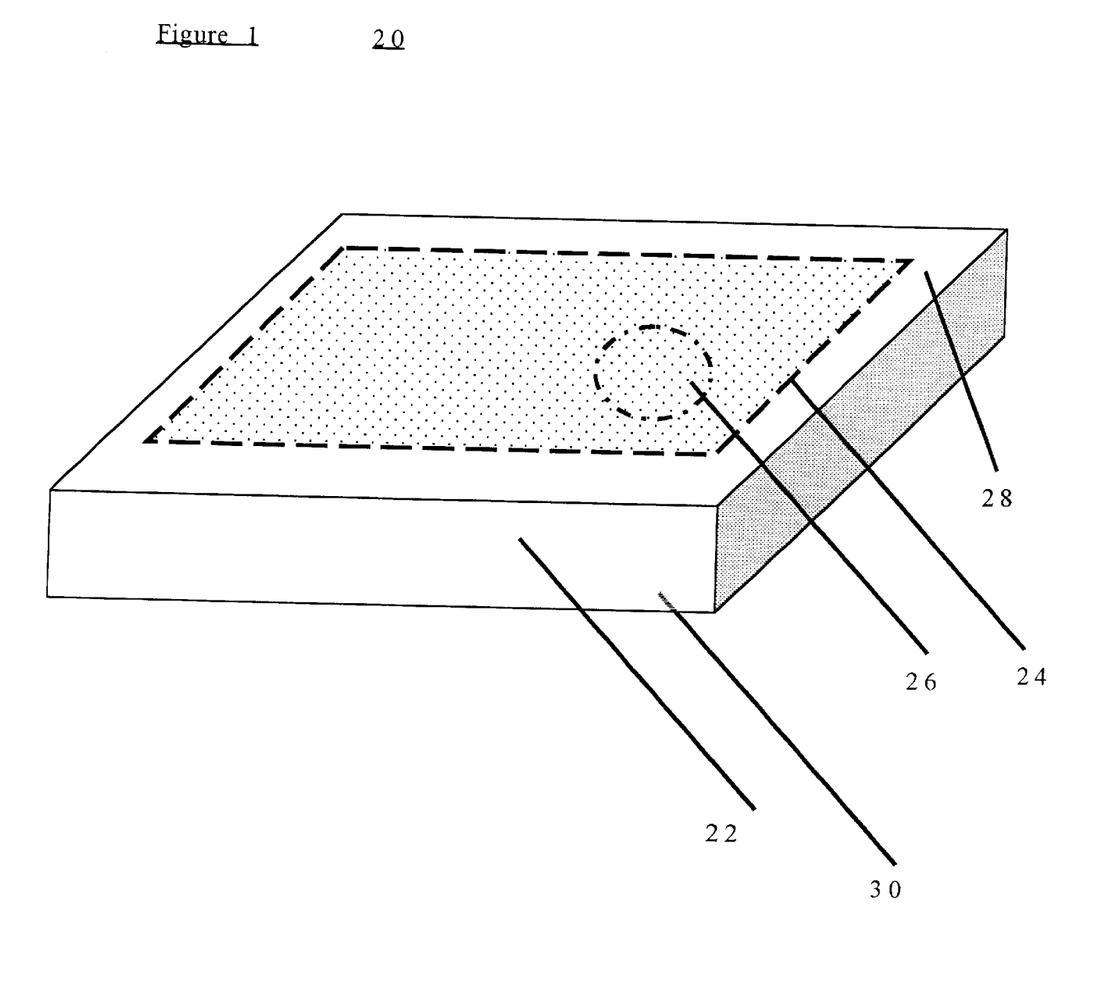
FIG. 1 is a perspective view of a cell carrier grid according to the present invention.
Figure 2:
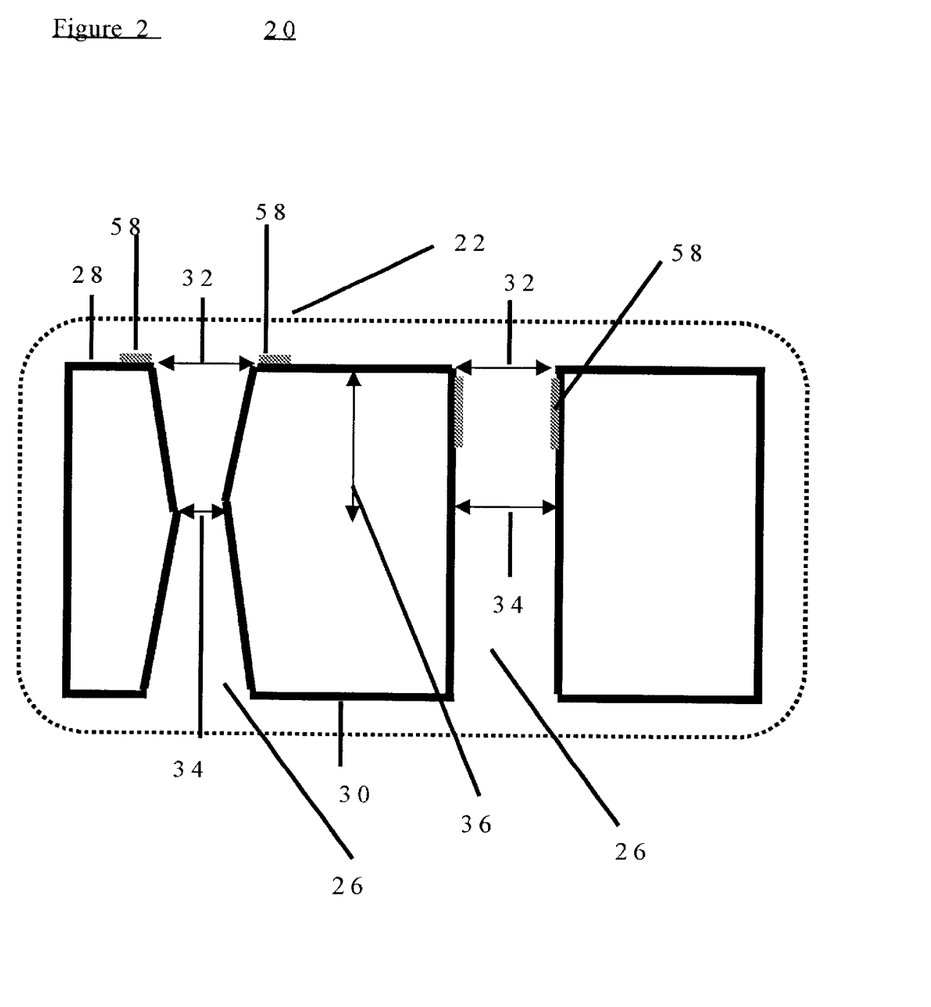
FIG. 2 is a is a cross sectional view of a cell carrier grid of the present invention showing alternate embodiments of holes therein.

FIG. 1 shows a cell carrier grid 20 capable of containing and retaining individual living cells in an array 24 of predefined discrete locations 26. Grid 20 may include, for example, a 100×100 2-dimensional array of holes 26. Each of holes 26 may be, for example, approximately 7 microns in diameter and spaced about 20 microns apart. The cell carrier grid 20 includes a body 22 that defines a first and a second outer surface (28 and 30). Body 22 has an ordered array 24 of holes 26 therethrough. Each of holes 26 communicates between first outer surface 28 and second outer surface 30. Grid 20 also includes an organizational plan (FIGS. 3a–d) applied to the positioning of holes 26 on body 22 such that a position of each of the holes is identifiable so that the holes form the array 24 of predefined discrete locations. Each of holes 26 is sized to contain at least a portion of an individual living cell therewithin (FIG. 2). To that end, each hole 26 has a first cross section 32 at first outer surface 28 of such dimensions that at least a portion of the individual living cell can pass through first cross section 32 without suffering substantial damage. Each of holes 26 also has a second cross section 34 at a level intermediate between the first and the second outer surfaces (28 and 30). In some cases this second cross section 34 is of such dimensions that the individual living cell cannot pass therethrough. In other cases, second cross section 34 is similar to first cross section 32. A height 36 is defined between first outer surface 28 and the level of second cross section 34 such that at least a portion of the individual living cell is containable within the hole, and the individual cell is retained therein. According to preferred embodiments of the invention, body 22 is designed and constructed such that the individual cells at least partially contained within holes 26 reside substantially in a single focal plane during analysis. This is achieved by imparting addition physical strength to grid 20, which also serves to prevent damage to grid 20 during use. As a result, accuracy of data collected from the individual cells within holes 26 is increased relative to prior art teachings.

Holding of cells in a single focal plane may be achieved, for example, by constructing body 22 of inherently rigid materials. In order to accomplish this, a Grid diagram at 1,000:1 is drawn on a computer. This diagram is a map of array 24 of holes 26 of grid 20. The diagram is then "inverted" and reduced by means of a computer program or by photography. This produces a reduced size negative of the grid. A further downscaling is achieved by projecting the negative through a microscope in the opposite direction, thereby receiving the desired picture on the side of the objective. This process produces a picture in which holes 26 are in the desired size (typically several microns). This picture of the grid is projected through the objective lens onto a thin metal paper (e.g. copper paper of 0.5-mm thickness) which is covered photo-emulsion. The emulsion changes its structure upon exposure to light. Typically several hundred grids are projected on a single sheet. The metal paper is then sequentially immersed in developer, fixer and a wash solution. This produces metal paper with fixed pictures of grids. The developing chemicals that are used, which stay on the metal paper, are non-conductive. The metal paper is then electroplated with a metal such as Nickel, Gold or Silver. The areas that are covered with the developmental chemicals are not coated in this process since they do not conduct electricity. This produces a metal picture of the projected. This process is repeated cyclically until holes 26 have the desired height 36 as detailed hereinbelow.

If, in each step the coating is applied in a bigger diameter over each of holes 26 conical wells are produced instead of cylindrical holes. If the diameter is held constant, cylindrical holes are produced.

Prior art grids are typically very thin. Since they are glued to the grid carrier as round circles, application of buffer to the grid carrier creates great pressure on the grid causing it to bulge. This bulging causes cells loaded on the grid to reside in a wide variety of focal planes causing inaccuracies in measurement. Bulging also effectively precludes automated retrieval of cells using programmed micromanipulators. .

Figure 5:
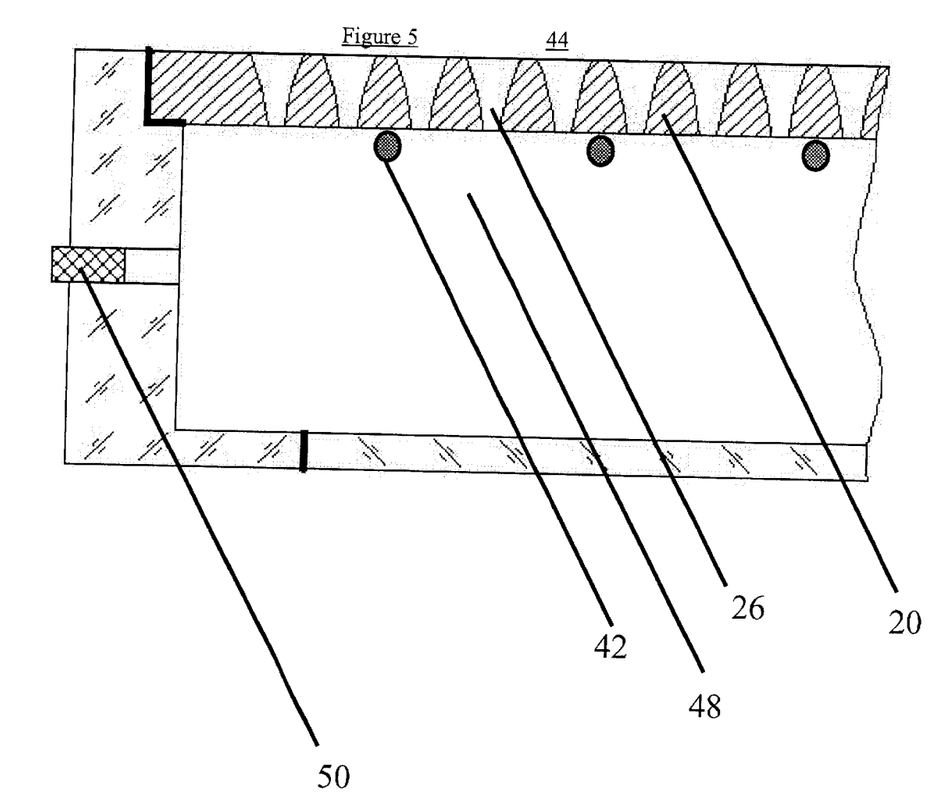
FIG. 5 is a cross sectional view of a cell carrier grid holder as in FIG. 4 in which supports for the grid are visible.

According to the present invention, bulging is prevented by starting with a thicker starting material. Alternately, or additionally thicker grids can be produced by repeating the electroplating process cyclically. Alternately or additionally, body 22 may be supported by at least one support 42 (FIG. 5) in order to keep individual cells contained within holes 26 substantially in a single focal plane during analysis. Supports 42 may run in more than one direction so that they intersect and reinforce one another. Supports might be organized, for example, in two pepedicular arrays, members of each array being parallel to one another. Alternately, supports might radiate outward from a single point, as spokes of a wheel.

According to preferred embodiments of the present invention, body 22 is at least partially coated with a biologically active material 58. Biologically active material 58 may be present within holes 56, or in proximity thereto, for example on first outer surface 28. Biologically active material 58 may include, for example, proteins, carbohydrates, nucleic acids, or lipids. Suitable proteins include, but are not limited to, antibodies, antigens, biotin, avidin, streptavidin, enzymes, ligands, receptors, mitogens, haptenes, a multimeric MHC-antigen complex and lectins. Suitable nucleic acids include, but are not limited DNA, RNA and derivatives thereof.

Suitable lipids include, but are not limited to Lysophosphatydilcholine (polar phospholipid) and OxLDL. It is known that preincubation with OxLDL can alter fluorescence of cells stained with FDA (N. Zurgil et al. (1999) Clin. Cardiol 22:5260–532). Coating of cell carrier grids is therefore an improvement upon this technique for assaying aterosclerosis which is currently being developed. Similarly Lysophosphatydilcholine has been demonstrated to activate lymphocytes (N Zurgil, unpublished results). Coating of cell carrier grids with this material is a significant improvement upon this technique for assaying arteriosclerosis because it brings individual cells into a micro-environment with a higher local concentration of reagent than that achievable using prior art teachings. In addition, supply of coated grids makes the assay simpler to perform by eliminating the need for incubation of cells with the material employed in the coating. This, in tern, reduces the level of skill required of a user of grid 20.

Figure 3A:
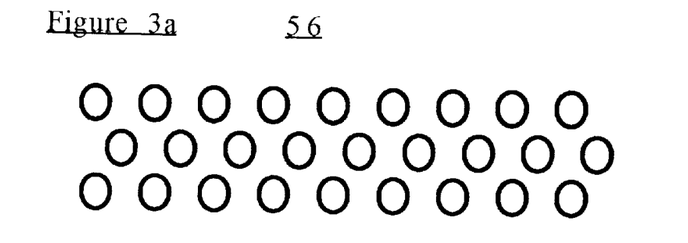
FIGS. 3a and 3b ahow two possible arrangements for an array of holes in a cell carrier grid according to the present invention.
Figure 3B:
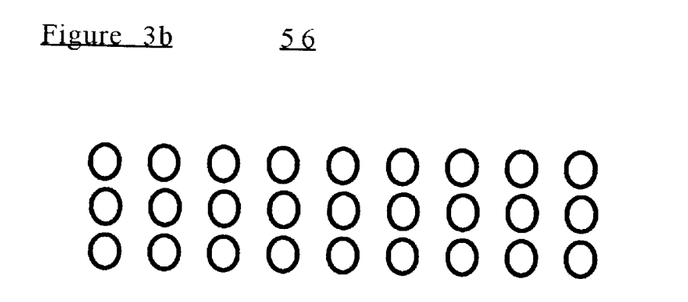
Figure 3C:
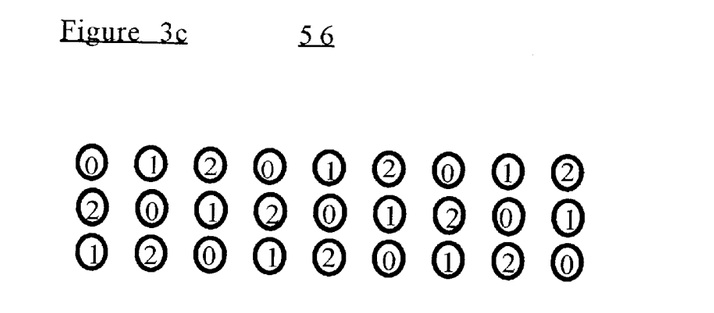
FIGS. 3c and 3d show two possible ways in which different holes might be coated with different biologically active materials while some holes remain uncoated.
Figure 3D:
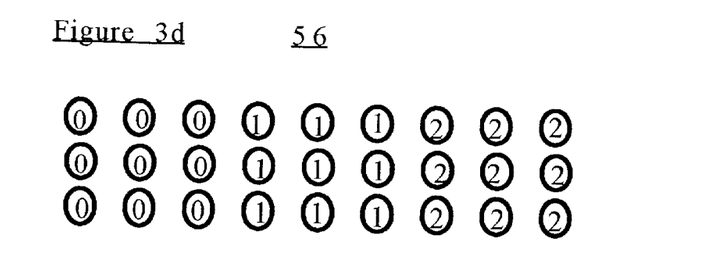

According to some embodiments of the invention, biologically active material 58 includes at least two separate biologically active materials, each of the at least two materials applied to a portion of holes 26 in array 24 of predefined discrete locations. FIGS. 3c and 3d show two possible arrangements of biologically active materials 1, 2, and 3 in holes 26. It should be noted that each biologically active material may include a combination of materials. For example, 3 may represent a combination of 1 and 2. Such an embodiment allows rapid and easy discovery of synergy between different coating materials. 0 is used to represent holes with no biologically active material. Such holes would typically serve to provide a baseline or negative control reading for an assay. This allows concurrent assay of more than one biologically active material on a single grid 20, something which is infeasible using prior art methods.

According to preferred embodiments of the present invention, body 22 is designed and constructed such that the individual cells contained within holes 26 are recoverable by a recovery device. This may be achieved, for example, by making height 36 less than the average radius of cells contained in holes 26. According to preferred embodiments of the invention at least 20%, more preferably at least 40%, most preferably at least 50% of the individual living cell contained within a hole extends beyond a plane defined by first outer surface 28 of body 22 to render the cell recoverable by a recovery device. Table 1 shows calculated well depths for cell types of research interest.

TABLE 1

Well depths required for various percentages of selected cell types to protrude from a well.

| Cell type | Avg. diameter | 20% depth | 40% depth | 50% depth |
|---|---|---|---|---|
| Lymphocytes | 11.5 micron | 9.2 micron | 6.9 micron | 5.75 micron |
| Monocytes | 16 micron | 12.8 micron | 9.6 micron | 8 micron |
| Neutrophils | 13 micron | 10.4 micron | 7.8 micron | 6.5 micron |
| Eosinophils | 14 micron | 11.2 micron | 8.4 micron | 7 micron |
| Basophils | 12 micron | 9.6 micron | 7.2 micron | 6 micron |
| platelets | 7 micron | 5.6 micron | 4.2 micron | 3.5 micron |

Figure 4:
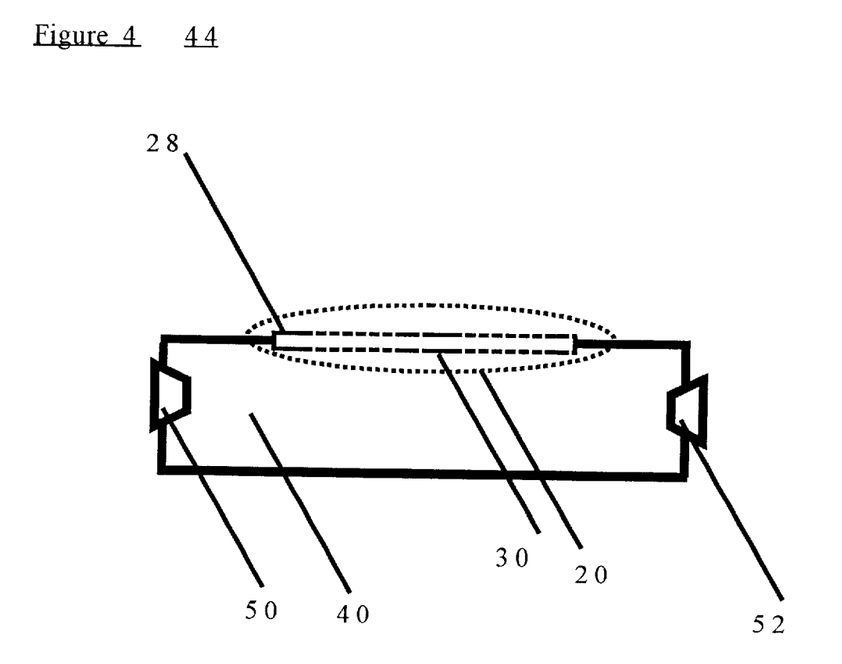
FIG. 4 is a cross sectional view of a cell carrier grid holder containing a cell carrier grid according to the present invention.

According to preferred embodiments of the invention cell carrier grid 20 further includes a holder 44 (FIG. 4) designed and constructed to facilitate manipulation of cell carrier grid 20. Holder 44 further allows application of suction through the holes in the grid such that cells in suspension applied to first outer surface 28 of grid 20 tend to move towards and into holes 26. Holder 44 further permits application and removal of solutions to cells residing in holes 26. Holder 44 includes a first port 50 and a second port 52, each communicating with a space 48 which contacts second outer surface 30 of grid 20. Ports 50 and 52 serve for introduction and removal of liquids into space 48 and relative flow rates therethrough can create suction through holes 26 in grid 20.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A cell carrier grid containing and retaining individual living cells in an array of predefined discrete locations, the cell carrier grid comprising;
    (a) a body that defines a first and a second outer surface, said body having an ordered array of holes therethrough, each of said holes communicating between said first outer surface and said second outer surface;
    (b) an organizational plan, said plan being applied to the positioning of said holes on said body such that a position of each of the holes is identifiable so that the holes form the array of predefined discrete locations;
    (c) wherein each of said holes is sized to contain at least a portion of an individual living cell therewithin, in that each hole has:
        (i) a first cross section at said first outer surface of such dimensions that at least a portion of said individual living cell can pass through said first cross section without suffering substantial damage;
        (ii) a second cross section at a level intermediate between said first and said second outer surfaces of such dimensions that the individual living cell cannot pass through the second cross section;
        (iii) a height between said first outer surface and the level of the second cross section such that at least a portion of said individual living cell is containable within said hole, and said individual cell is retained therein;
    wherein said body is designed and constructed such that said individual cells contained within said holes reside substantially in a single focal plane during analysis; and
    wherein accuracy of data collected from said individual cells within said holes is increased because said cells reside substantially in a single focal plane.

2. The cell carrier grid of claim 1, wherein said body is inherently rigid, such that said individual cells contained within said holes reside substantially in a single focal plane during analysis.

3. The cell carrier grid of claim 1, wherein said body is supported by at least one support, such that said individual cells contained within said holes reside substantially in a single focal plane during analysis.

4. The cell carrier grid of claim 1, further comprising:
(d) a holder, said holder designed and constructed to:
  (i) facilitate manipulation of the cell carrier grid;
  (ii) allow application of suction through said holes in the grid such that cells in suspension applied to said first outer surface of the grid tend to move towards and into said holes;
  (iii) permit application and removal of solutions to cells residing in said holes.

5. A cell carrier grid containing and retaining individual living cells in an array of predefined discrete locations, the cell carrier grid comprising;
(a) a body that defines a first and a second outer surface, said body having an ordered array of holes therethrough, each of said holes communicating between said first outer surface and said second outer surface;
(b) an organizational plan, said plan being applied to the positioning of said holes on said body such that a position of each of the holes is identifiable so that the holes form the array of predefined discrete locations;
c) wherein each of said holes is sized to contain at least a portion of an individual living cell therewithin, in that each hole has:
  (i) a first cross section at said first outer surface of such dimensions that at least a portion of said individual living cell can pass through said first cross section without suffering substantial damage;
  (ii) a second cross section at a level intermediate between said first and said second outer surfaces, said second cross section being no greater in size than said first cross section;
  (iii) a height between said first outer surface and the level of the second cross section such that at least a portion of said individual living cell is containable within said hole, and said individual cell is retained therein;
wherein said body is at least partially coated with a biologically active material.

6. The cell carrier grid of claim 5, wherein said biologically active material is at least one material selected from the group consisting of a protein, a carbohydrate, a nucleic acid, and a lipid.

7. The cell carrier grid of claim 6, wherein said protein is selected from the group consisting of an antibody, an antigen, biotin, avidin, streptavidin, an enzyme, a ligand, a receptor, a mitogen, a haptene, a multimeric MHC-antigen complex and a lectin.

8. The cell carrier grid of claim 6, wherein said nucleic acid is selected from the group consisting of DNA, RNA and derivatives thereof.

9. The cell carrier grid of claim 6, wherein said lipid is selected from the group consisting of Lysophosphatydilcholine and oxidized low density lipid (OxLDL).

10. The cell carrier grid of claim 5, wherein said biologically active material is used to coat said body at a location selected from the group consisting of within said holes and adjacent to said holes.

11. The cell carrier grid of claim 5, wherein said biologically active material comprises at least two separate biologically active materials, each of said at least two materials applied to a portion of said holes comprising the array of predefined discrete locations.

12. The cell carrier grid of claim 5, further comprising:
(d) a holder, said holder designed and constructed to:
  (i) facilitate manipulation of the cell carrier grid;
  (ii) allow application of suction through said holes in the grid such that cells in suspension applied to said first outer surface of the grid tend to move towards and into said holes;
  (iii) permit application and removal of solutions to cells residing in said holes.

13. A cell carrier grid containing and retaining individual living cells in an array of predefined discrete locations, the cell carrier grid comprising;
(a) a body that defines a first and a second outer surface, said body having an ordered array of holes therethrough, each of said holes communicating between said first outer surface and said second outer surface;
(b) an organizational plan, said plan being applied to the positioning of said holes on said body such that a position of each of the holes is identifiable so that the holes form the array of predefined discrete locations;
(c) wherein each of said holes is sized to contain at least a portion of an individual living cell therewithin, in that each hole has:
  (i) a first cross section at said first outer surface of such dimensions that at least a portion of said individual living cell can pass through said first cross section without suffering substantial damage;
  (ii) a second cross section at a level intermediate between said first and said second outer surfaces, said second cross section being no greater in size than said first cross section;
  (iii) a height between said first outer surface and the level of the second cross section such that at least a portion of said individual living cell is containable within said hole, and said individual cell is retained therein;
wherein said body is designed and constructed such that said individual cells contained within said holes are recoverable by a recovery device.

14. The cell carrier grid of claim 13, wherein at least 20% of said individual living cell contained within a hole extends beyond a plane defined by said first outer surface to render said cell recoverable by a recovery device.

15. The cell carrier grid of claim 13, wherein at least 40% of said individual living cell contained within a hole extends beyond a plane defined by said first outer surface to render said cell recoverable by a recovery device.

16. The cell carrier grid of claim 13, wherein at least 50% of said individual living cell contained within a hole extends beyond a plane defined by said first outer surface to render said cell recoverable by a recovery device.

17. The cell carrier grid of claim 13, further comprising:
(d) a holder, said holder designed and constructed to:
  (i) facilitate manipulation of the cell carrier grid;
  (ii) allow application of suction through said holes in the grid such that cells in suspension applied to said first outer surface of the grid tend to move towards and into said holes;
  (iii) permit application and removal of solutions to cells residing in said holes.

* * * * *

UNITED STATES PATENT AND TRADEMARK OFFICE
CERTIFICATE OF CORRECTION

PATENT NO.   : 6,495,340 B2
DATED        : December 17, 2002
INVENTOR(S)  : Huberman et al.

It is certified that error appears in the above-identified patent and that said Letters Patent is hereby corrected as shown below:

Title page,
Item [75], change "Yal" to -- Yael --

Signed and Sealed this

Twenty-second Day of April, 2003

JAMES E. ROGAN
*Director of the United States Patent and Trademark Office*